(12) United States Patent
Samadani et al.

(10) Patent No.: US 12,140,788 B2
(45) Date of Patent: Nov. 12, 2024

(54) DEVICES AND METHODS FOR SPATIALLY CONTROLLABLE ILLUMINATION

(71) Applicant: Intuitive Surgical Operations, Inc., Sunnyvale, CA (US)

(72) Inventors: Ramin Samadani, Menlo Park, CA (US); Jonathan D. Halderman, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 79 days.

(21) Appl. No.: 17/945,046

(22) Filed: Sep. 14, 2022

(65) Prior Publication Data

US 2023/0084030 A1    Mar. 16, 2023

Related U.S. Application Data

(60) Provisional application No. 63/244,620, filed on Sep. 15, 2021.

(51) Int. Cl.
| | |
|---|---|
| *A61B 1/06* | (2006.01) |
| *A61B 1/00* | (2006.01) |
| *F21V 8/00* | (2006.01) |
| *G06V 10/25* | (2022.01) |
| *H04N 23/50* | (2023.01) |
| *H04N 23/74* | (2023.01) |

(52) U.S. Cl.
CPC ........ *G02B 6/0006* (2013.01); *A61B 1/00009* (2013.01); *A61B 1/0655* (2022.02); *G02B 6/0008* (2013.01); *H04N 23/74* (2023.01); *G06V 10/25* (2022.01); *G06V 2201/03* (2022.01); *H04N 23/555* (2023.01)

(58) Field of Classification Search
CPC ............... G02B 6/0006; G02B 6/0008; A61B 1/00009; A61B 1/0655; A61B 1/045; A61B 1/0605; A61B 1/0627; A61B 1/0646; H04N 23/74; H04N 23/555; H04N 23/56; H04N 23/61; H04N 23/611; G06V 10/25; G06V 2201/03
See application file for complete search history.

(56) References Cited

U.S. PATENT DOCUMENTS

| | | | |
|---|---|---|---|
| 10,254,534 B2* | 4/2019 | Caravaca-Aguirre | ....................... H04N 23/56 |
| 2008/0058629 A1* | 3/2008 | Seibel | ...................... A61B 1/07 600/368 |
| 2011/0115882 A1* | 5/2011 | Shahinian | .......... A61B 1/00193 348/E13.001 |
| 2013/0050454 A1* | 2/2013 | Ogasawara | ........ A61B 1/00009 348/E7.085 |

(Continued)

OTHER PUBLICATIONS

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

*Primary Examiner* — Jared Walker
(74) *Attorney, Agent, or Firm* — Schwegman, Lundberg & Woessner, P.A.

(57) ABSTRACT

Described herein are devices, systems, and methods for illumination of a target that provide control over the beam divergence, beam shape, and/or direction of the illumination beam. Such illumination beam control may be based on images of the target, and may serve to direct light at one or more regions of interest.

13 Claims, 12 Drawing Sheets

(56) References Cited

U.S. PATENT DOCUMENTS

| | | | |
|---|---|---|---|
| 2013/0314520 A1* | 11/2013 | Ishihara | A61B 1/043 |
| | | | 348/68 |
| 2013/0324858 A1* | 12/2013 | Xu | A61B 5/0068 |
| | | | 600/478 |
| 2016/0278678 A1* | 9/2016 | Valdes | A61B 5/14546 |
| 2018/0302542 A1* | 10/2018 | Masumura | G02F 1/136277 |
| 2018/0367786 A1* | 12/2018 | Furst | A61C 9/006 |
| 2019/0369650 A1* | 12/2019 | Swanson | G02B 6/04 |
| 2020/0060528 A1* | 2/2020 | Akimoto | G06T 7/579 |
| 2020/0060531 A1* | 2/2020 | Yamazaki | A61B 1/0684 |
| 2020/0082510 A1* | 3/2020 | Wang | H04N 23/56 |
| 2020/0154029 A1* | 5/2020 | Mitsui | G06T 7/90 |
| 2020/0154038 A1* | 5/2020 | Sakamoto | H04N 23/80 |
| 2020/0214547 A1* | 7/2020 | Aoyama | A61B 1/0646 |
| 2021/0044750 A1* | 2/2021 | Kamon | A61B 1/005 |
| 2021/0145248 A1* | 5/2021 | Ito | A61B 1/000094 |
| 2021/0223525 A1* | 7/2021 | Lv | G02B 21/008 |
| 2021/0235980 A1* | 8/2021 | Oosake | G06N 3/08 |
| 2021/0393109 A1* | 12/2021 | Iketani | A61B 1/000094 |
| 2022/0117477 A1* | 4/2022 | Wang | A61B 1/07 |
| 2022/0286627 A1* | 9/2022 | Steiner | G02B 23/2461 |
| 2022/0287554 A1* | 9/2022 | Ito | A61B 1/05 |

* cited by examiner

DEVICES AND METHODS FOR SPATIALLY CONTROLLABLE ILLUMINATION

CLAIM OF PRIORITY

This application claims the benefit of priority under 35 U.S.C. § 119(e) to U.S. Provisional Patent Application Ser. No. 63/244,620, filed on Sep. 5, 2021, which is incorporated by reference herein in its entirety.

TECHNICAL FIELD

This disclosure relates generally to illumination, for example, as used in endoscopy or borescope inspections.

BACKGROUND

During minimally invasive surgical or other medical procedures, an anatomical target inside the body may be accessed via a rigid or flexible tube that is inserted into the body via a, small incision or natural orifice and guided to the target. In this context, target imaging for diagnosis or monitoring during a procedure can be accomplished with a fiber-optic endoscope including a camera located at the distal end of the tube, and an optical fiber or fiber bundle running from the proximal end to the distal end of the tube to deliver light from a light source (e.g., outside the body) to the distal end for target illumination. The camera may capture light scattered or reflected off the target, e.g., at the illumination wavelength (e.g., in the visible regime). Alternatively, in fluorescence imaging, the camera may capture light at a fluorescence wavelength emitted by a fluorescent dye in the target upon target illumination with light at a shorter excitation wavelength. Fluorescence imaging is often employed, for example, to detect and avoid damage to sensitive anatomical structures (e.g., ureters), to detect treatment targets (e.g., sentinel lymph nodes in cancer therapy), or to estimate perfusion over an anatomical region to avoid anastomotic leaks (e.g., in gastrointestinal surgery). When different types of procedures utilize the same illumination profile, this may result in the camera capturing less than optimal information for the different procedures.

SUMMARY

Described herein are devices, systems, and methods for illumination of a target, such as an interior target. Various applications (e.g., surgical or other medical procedures) may differ significantly in the optimal illumination profile. For example, uniform illumination of an area may be desirable for gauging perfusion, whereas a narrow illumination beam may be preferable to detect and monitor specific anatomic structures, especially if signal levels are low. Accordingly, there is no one-size-fits-all device configuration that performs optimally over a wide range of illumination applications. To address this issue, the beam divergence, beam shape, and/or direction of the illumination beam may be controlled, thereby allowing the illumination profile to be tailored to the specific illumination target or application. In general, the target can be illuminated by irradiation with light at any wavelength. Applications of target illumination include both fluorescent excitation and irradiation with light of the same wavelength as is detected to generate an image of the target. "Endoillumination" is herein understood as the illumination of a substantially enclosed target inside an animate or inanimate object by an illumination beam source located at the distal end of a device inserted into the object through an opening and generally controlled from outside the object. The illumination beam source may, for example, be or include the distal end of an optical fiber or fiber bundle that receives light at its proximal end from an external light source. Alternatively, the illumination beam source may include light emitters (e.g., light emitting diodes (LEDs)) mounted on the distal end of a rigid or flexible tube or shaft and connected, via electrical wires, to an external power source and/or controller. A device including an illumination beam source, associated optical fiber or electrical lines, and any tube, shaft, or the like providing mechanical structure for guiding the illumination beam source into position is referred to as an illumination device. While examples of illumination devices described herein are generally adapted for use in endoillumination, it is to be understood that the illumination device need not be limited in their use to endoillumination, but could also find application in the illumination of external targets.

In various examples, the illumination device is integrated with or forms part of an endoscope or, more generally, a borescope. For example, an endoscope or borescope may include a tube with a distally mounted camera for imaging the target, along with optical fiber(s) running through the tube to provide for illumination. In alternative examples, the illumination device may be a stand-alone device that serves to illuminate the target, and any imaging functionality may be provided separately, e.g., by an endoscope or borescope. Endoscopes and borescopes, as the terms are generally understood, differ in their range of applications: endoscopes (which are a subset of borescopes) serve specifically to image anatomical targets inside animate objects (e.g., human patients or animals), whereas borescopes may also be used for non-medical purposes, such as for inspection of targets at difficult-to-access locations inside inanimate objects like pipes, engines or other machines, etc. For purposes of the examples described herein, where reference is made to an endoscope, application to a borescope is generally also contemplated.

Spatial control over the illumination beam, in accordance with this disclosure, can be achieved in various ways. In some examples, the illumination beam output at the distal end of a fiber-optic illumination device is manipulated via the light input into the optical fiber or fiber bundle at the proximal end. For example, a light source that generates and couples light into the proximal fiber end may be operable to adjust the maximum angle, relative to the fiber axis, at which light is coupled into the fiber, whose sine is herein also referred to as the "effective numerical aperture" of the fiber, thereby adjusting the beam divergence at the fiber output. Similarly, the light source may be operable to adjust the angular distribution of the input light and, thus, the angular distribution of the illumination beam at the fiber output: Alternatively to manipulating the light at the fiber input, the illumination beam can also be manipulated at the fiber output. The illumination device may, for instance, be equipped, at the distal end, with an adjustable lens system that allows controlling the beam divergence, with a movable refractive or reflective element or acousto-optic modulator that enables changing the beam direction, or with a beam shaper to facilitate modifying the intensity distribution of the beam. The intensity distribution can also be manipulated by scanning the beam continuously across an area including the target while simultaneously, and in a coordinate manner, changing the beam intensity (e.g., via control of the light source at the fiber input).

Yet another approach to controlling the illumination beam utilizes an illumination device with multiple individually addressable fiber bundles that generate beams in different directions. At the distal end, the fiber bundles may, for example, be oriented with their axes in different fixed directions, terminate in faces oriented in different directions, or be individually physically movable (e.g., by micromechanical systems) to adjust their respective pointing directions. As an alternative to the use of optical fiber bundles, it is also possible to achieve illumination with a device that includes multiple individually addressable light emitters (e.g., LEDs) configured to emit beams in different directions. Whether generated by light emitters at the distal end of the illumination device or emanating from fiber bundles, the multiple beams, which are generally narrower than a single illumination beam and herein also referred to as "microbeams," may be individually turned on or off, or adjusted in intensity, to generate an overall beam of the desired intensity distribution.

Using these or similar illumination devices that provide control over the illumination beam divergence, direction, and/or shape, light can be concentrated (that is, the illumination intensity can be deliberately increased) in regions where the light is needed more, such as in regions of anatomical interest, or in regions that are otherwise subject to lower signal levels, e.g., as a result of lower fluorescent marker levels or of greater intensity fall-off due to their location at greater depths. In various examples, the regions to be preferentially illuminated may be determined based on human feedback and/or automated control input. For example, in some examples, a user e.g., a human operator) of an imaging system including the illumination device may explicitly define a region of interest within a user interface. In other examples, the beam divergence is automatically adjusted as the user zooms in or out within a field of view of an endoscope/borescope camera to match the field of illumination to the zoom level, or the beam is automatically steered as the user moves a zoomed-in region across the field of view to move the illuminating beam along with that region. In further examples, the camera images may be analyzed automatically to identify a (for example, anatomical) structure of interest, or an image region suffering from low signal to noise (SNR), and the light is directed at the identified structure or low-SNR region. It is also possible to determine, based on the camera image or by other means, the depth across an illuminated scene, and increase the relative radial intensity of the beam towards regions located at greater depth to compensate for the radial intensity fall-off of the illuminating light.

The preceding summary is intended to provide a basic overview of the disclosed subject matter, but is not an extensive summary of all contemplated embodiments, nor is it intended to identify key or critical elements or delineate the scope of such embodiments.

BRIEF DESCRIPTION OF THE DRAWINGS

The foregoing will be more readily understood from the following description of various example examples, in particular, when taken in conjunction with the accompanying drawings, in which.

DESCRIPTION

The illumination devices, systems, and methods disclosed herein provide various approaches to spatially controlling the illumination of a target via control of the direction of the illumination beam, the beam divergence, and/or the beam shape. The term "beam shape" herein denotes the transverse intensity distribution of the beam (measured in terms of the radiant flux or power, in watts, per unit area in a plane orthogonal to the direction of beam propagation), or equivalently, the radiant intensity distribution (measured in terms of the radiant flux or power per unit solid angle). In general, spatial illumination control in accordance herewith is informed by processing and analysis of images of the target and/or user feedback.

Figure 1:
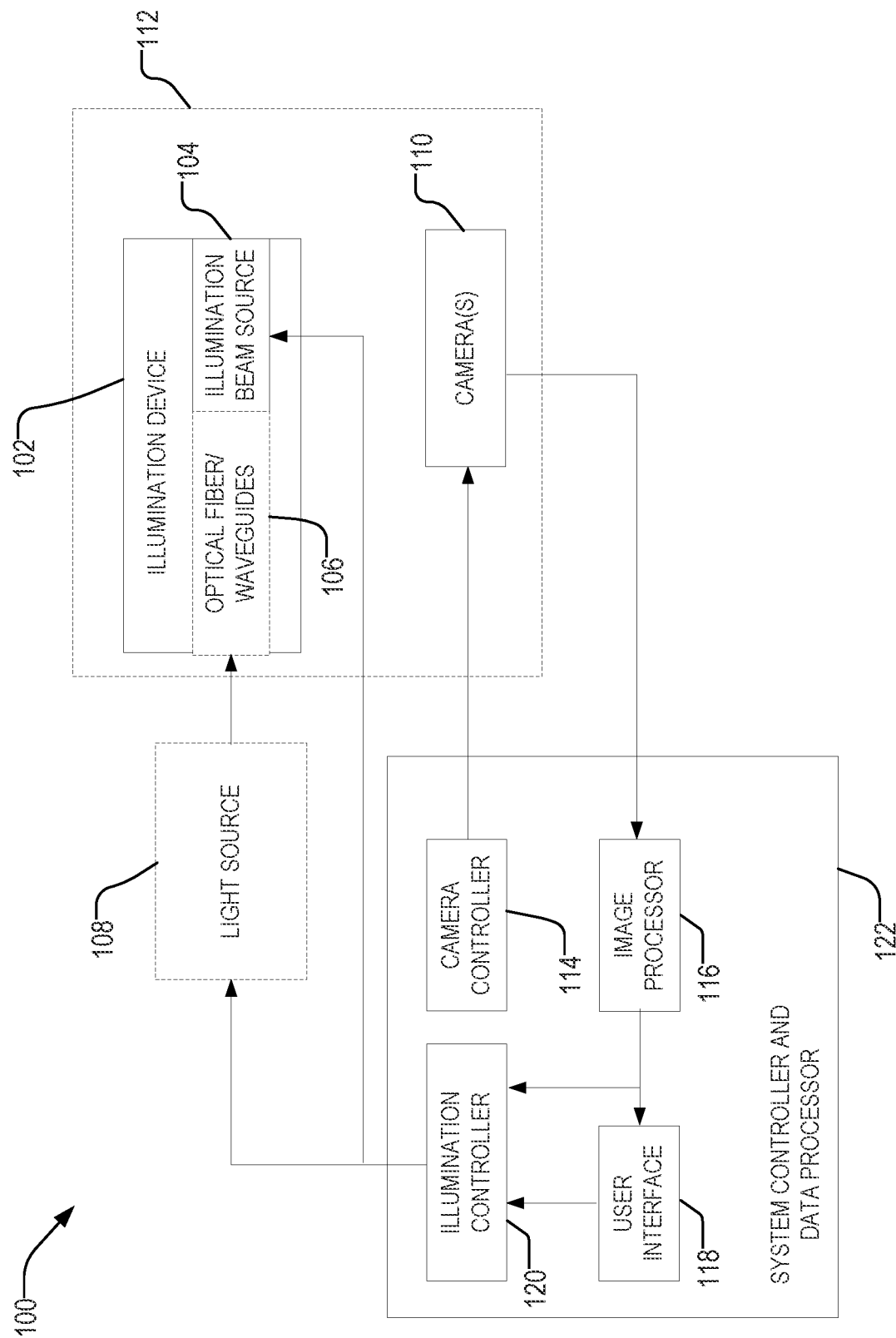
FIG. 1 is a block diagram of an example system for endoscopy and spatially controlled illumination.

FIG. 1 is a block diagram of an example system 100 for endoscopy and spatially-controlled illumination. The system 100 includes an illumination device 102 with an illumination beam source 104 at its distal end. Light may be generated by the illumination beam source 104 itself, or guided to the illumination beam source 104 via optical fiber 106 or, more generally, one or more optical waveguides, from a light source 108 located, for example, at the proximal end. The illumination device 102 generally includes a long structure or housing, such as a rigid or flexible shaft, that enables guiding the illumination beam source 104, which may be mounted in or on its distal end, into position. A flexible shaft, for instance, allows snaking the illumination beam source 104 through small openings and along narrow lumina. In different examples, the shaft may be either solid or hollow. A hollow shaft may serve to house optical fibers or electrical wires connecting the illumination beam source 104 to an apparatus located at the proximal end of the illumination device 102.

Further, the system 100 may include one or more cameras 110, each generally including an image sensor (such as a charged-coupled device (CCD) sensor array) and associated imaging optics, for imaging the target. In use, the illumination beam source 104 and camera(s) 110 may be positioned and oriented such that the illuminated region overlaps with the field of view of the camera(s) 110. The cameras 110 and illumination device 102 may be integrated in a single device 112 (e.g., an endoscope or borescope as illustrated in FIGS. 2B and 6B). In some examples, the camera(s) 110 and illumination beam source 104 may be located side by side at the distal end of the device 112. In some examples, the illumination device 102 and camera(s) may be housed in different devices. For example, the target may be illuminated and imaged from different respective angles, using different respective devices.

The camera(s) 110 are communicatively coupled to a camera controller 114 for operating the camera(s) 110 and an image processor 116 for processing the signals read out from the image sensor(s) to generate images for display to a user within a user interface 118 and/or for further analysis. The system 100 may include an illumination controller 120 which, depending on the particular example, is communicatively coupled to and controls the operation of the illumination beam source 104 within the illumination device 102, the light source 108, or both. Communications between the camera 110 and the camera controller 114 and image processor 116 and between the illumination controller 120 and the illumination beam source 104 or light source 108 may generally take place over an optical connection, an electrically wired connection, a wireless connection, or the like. Wireless connections may be established, for instance, via radio frequency (RF) connections. In some examples, wireless connections may be established via Bluetooth or WiFi.

The illumination controller 120 may be communicatively coupled to, and responsive to input received from, the image processor 116 and/or the user interface 118. For instance, the image processor 116 may perform automated image analysis, e.g., to detect the target or specific structures of interest within the image, to measure SNR across the image, and/or to determine depth across the image. Depth determination may be based, for instance, on parallax measured in stereo images, that is, pairs of images taken of the imaged scene simultaneously from slightly different angles with a pair of cameras 110. The images may alternatively be manually analyzed within the user interface 118 by a user, e.g., a surgeon operating the system 100. The user may, for example, provide user input regarding desired zoom levels, regions of interest, etc. User input and automated analysis may also be used in conjunction. For example, the user may indicate a general region of interest, and the image processor 116 may identify a structure within that region; or conversely, the user may select a structure of interest among multiple structures automatically identified within the image. Based on the automated image analysis and/or user feedback, the illumination controller 120 may cause the light of the illumination beam to be directed toward certain identified areas, such as on structures of interest or within regions affected by low SNR or high intensity fall-off with depth, for example. As a result of such targeted illumination, the light may be concentrated in the identified areas, e.g., with other regions being illuminated, if at all, with significantly lower intensity.

The camera controller 114, image processor 116, user interface 118, and/or illumination controller 120 may be implemented in a single device or with multiple intercommunicating devices, hereinafter referred to collectively as the system controller and data processor 122. The system controller and data processor 122 generally employs a suitable combination of computing hardware and/or software, e.g., including one or more general-purpose processors executing program instructions stored in memory, one or more special-purpose processors (such as, e.g., a graphical-processing unit (GPU), field-programmable gate array (FPG), application-specific integrated circuit (ASIC), or digital signal processor (DSP)), and/or hardwired, configurable, or programmable analog or digital electronic circuitry. In some examples, the system controller and data processor 122 implements the control and image-processing functionality as well as the user interface 118 with software modules running on a general-purpose computer (or a networked cluster of computers). In addition to one or more central processing units (CPUs) and optional hardware accelerators (e.g., a GPU or ASIC), as can be customized to perform complex, but fixed processing tasks, the computer (cluster) generally includes one or more machine-readable storage devices, which may include both volatile memory (such as random-access memory (RAM)) and non-volatile memory (such as read-only memory (ROM), flash memory, or magnetic or optical computer storage devices). Further, the computer(s) may include user-interface hardware, such as a display device for display of the images, and a keyboard, mouse, touchpad, or similar user input device. The display device may optionally be a touch screen display device that acts as the user input device.

Having provided an overview of a system for spatially controlled illumination, various examples will now be described.

Figure 2A:
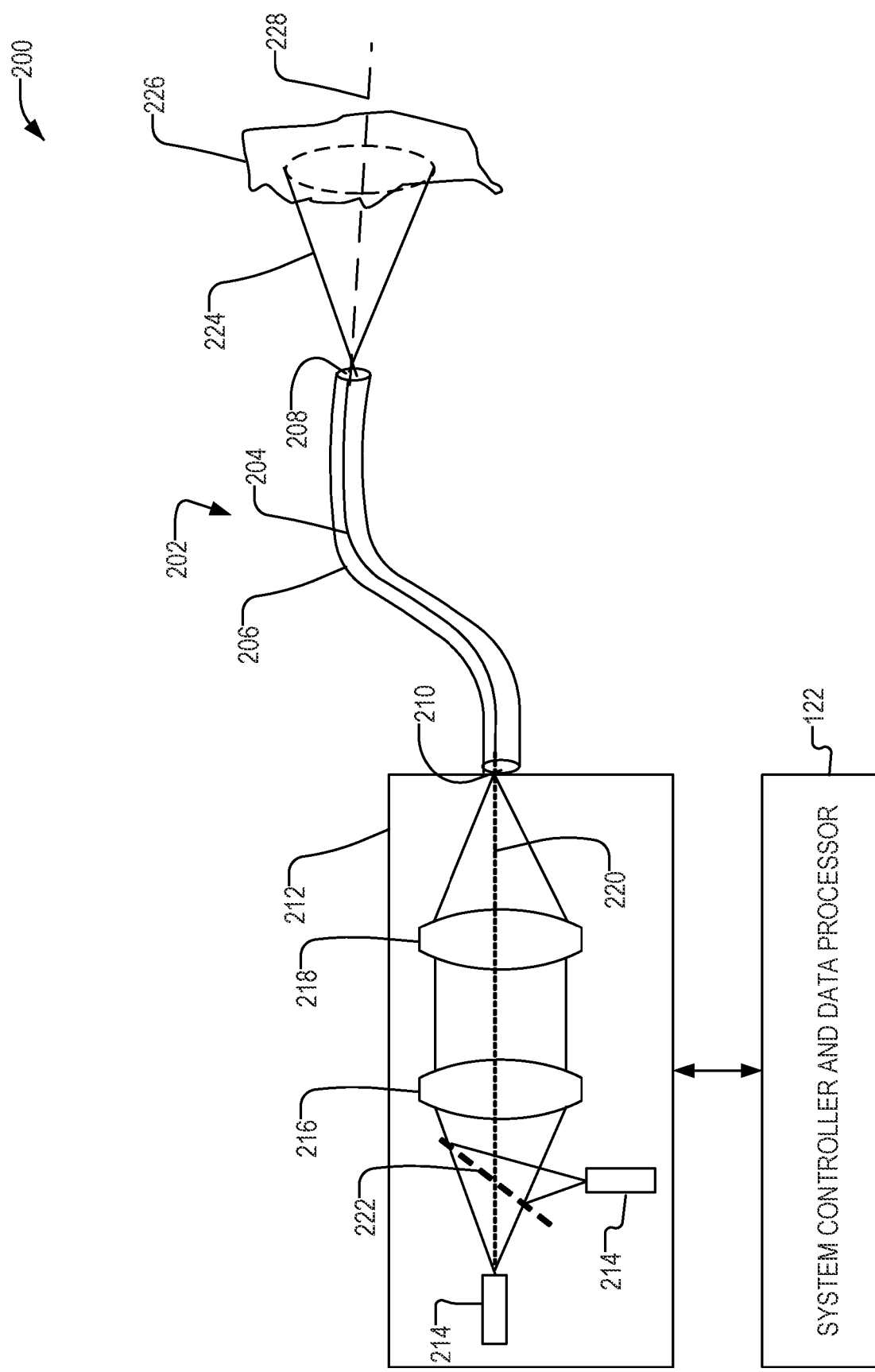
FIG. 2A is a schematic diagram of an example fiber-optic illumination system.
Figure 2B:
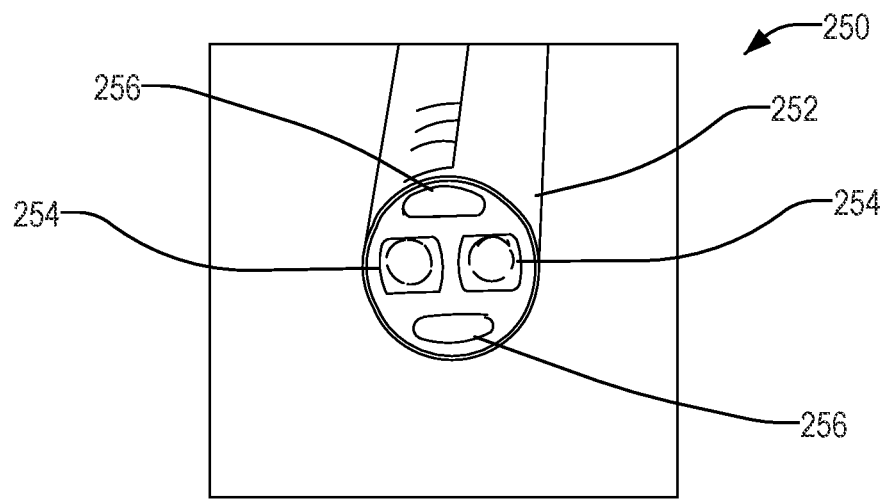
FIG. 2B is a front schematic view of the distal end of an example endoscope as may be used in the system of FIG. 2A.

FIG. 2A is a schematic diagram of an example fiber-optic illumination system 200. The system 200 includes a fiber-optic illumination device 202 (constituting an example implementation of device 102) formed by one or more optical fibers or fiber bundles (hereinafter generically "optical fiber") 204 housed in a rigid or flexible tube 206, such as, e.g., a catheter. One or more cameras may be integrated with the illumination device 202 at or near the distal end 208 of the fiber 204 to collectively form an endoscope, e.g., as shown in FIG. 2B.

The illumination system 200 further includes, at the proximal end 210 of the optical fiber 204, a light source 212 (constituting an example of light source 108) configured to generate and couple light into the optical fiber 204. The light source 212 includes one or more light emitters 214, such as lasers (e.g., diode lasers), light emitting diodes (LEDs), or broadband light sources. The light source 212 may optionally include optics to direct the light into the optical fiber 204. As shown, the optics may, for instance, include a collimating optic 216 that turns a diverging beam of light received from the light emitter(s) 214 into a collimated beam of parallel light, as well as a focusing optic 218 that focuses the light down onto a region at or very near the input, or proximal end 210, of the optical fiber 204. The fiber input may be placed substantially at the focal plane of the focusing optic 218. The collimating and focusing optics 216, 218 may, as shown, share a common optical axis 220 with the optical fiber 204 at its proximal end 210 as well as with a diverging beam of light received by the collimating optic 216 and the focused beam of light entering the optical fiber 204. The collimating and focusing optics 216, 218 may generally be or include refractive and/or reflective optical components, such as lenses and/or (spherical or parabolic) mirrors. To facilitate illumination at different wavelengths (e.g., in the visible for background illumination and in the infrared, visible, or ultraviolet for fluorescence excitation), the collimating optic 216 may receive and combine light from multiple light emitters 214 emitting at different wavelengths, with one or more beam splitters 222 in the optical path serving to direct the light from the emitters 214 towards the collimating optic 216.

The light coupled by the light source 212 into the fiber 204 at the proximal end 210 is guided to the distal end 208, where it exits the fiber 204, forming a diverging beam, herein the "illumination beam" 224. In use, the illumination beam 224 is directed at a target 226. The distal fiber end 208 may function as a point light source for illumination of the target 226. In accordance with various examples, the light source 212 and/or illumination device 202 may include optical components for varying the beam divergence, beam shape, and/or direction of the illumination beam 224 relative to the a longitudinal axis 228 of the illumination device 202 at its distal end (e.g., corresponding to the optical axis of the optical fiber 204 at the distal fiber end 208, or in the case of multiple optical fibers or fiber bundles pointing in different directions, to an average of the respective optical axes) responsive to an illumination controller 120.

FIG. 2B is a front view of the distal end of an example endoscope 250 as may be used in the system 200 of FIG. 2A. This endoscope 250 includes a tube 252 housing two cameras 254 placed side by side along a diameter of the tube 252 (e.g., for stereo imaging), and two optical fiber bundles 256 (collectively constituting optical fiber 204) placed above and below the cameras 254, respectively. In some examples, the dimensions of the cameras 254 and fiber bundles 256 are on the order of a few millimeters. In some examples, the tube 252 may have a diameter of approximately 8.8 mm or approximately 12 mm. The fiber bundles 256 may include tens, hundreds, or thousands of individual optical fibers. In some examples, each fiber bundle 256 may include between 1400 and 3000 optical fibers. Each individual fiber may have a core diameter between 30 and 50 μm, and a cladding having a thickness of about 2 μm. Using a bundle of many small-diameter fibers, in place of one larger-diameter fiber, can serve to achieve the mechanical flexibility needed to reach otherwise inaccessible targets in many clinical scenarios.

In an endoscope with integrated fiber-optic illumination (e.g., endoscope 250), the camera(s) and distal end 208 of the optical fiber 204 may be configured, in their relative position and orientation, such that the illumination beam is generally within, or at least substantially overlaps with, the field of view of the camera(s). In examples with a fixed illumination beam direction and variable beam divergence, the endoscope may be configured such that the optical axis of the camera imaging optics (e.g., in endoscope 250 taken to be an axis parallel to and midway between the optical axes associated with the two cameras 254) and the optical axis of the distal fiber end (e.g., in endoscope 250 taken to be an axis positioned midway between and oriented in a direction midway between the directions of the two fiber bundles 256) substantially coincide (allowing for some small parallel displacement due to spatial constraints) to achieve "coaxial illumination," and that the illumination field for the maximum attainable illumination beam divergence substantially corresponds to the field of view of the camera(s) (allowing for some slight deviation around the margins). In examples with variable beam direction, the endoscope may be configured such that the region over which the beam can be scanned substantially corresponds to the field of view of the camera(s).

The divergence of the illumination beam 224 output at the distal end 208 of the optical fiber 204, measured in terms of its angular extent relative to the fiber axis, is equal to the angular extent of light that enters the optical fiber 204 at the proximal end 210 and that is guided along the fiber core by total internal reflection. The maximum angle of incidence at the fiber input at which light rays are still guided rays is the acceptance angle α of the optical fiber 204; light at larger angles of incidence is generally lost to the cladding and does not reach the distal fiber end. The sine of the acceptance angle α, known as the numerical aperture NA of the fiber, is given by $NA = \sin \alpha = \sqrt{n_1^2 - n_2^2}$, where $n_1$ and $n_2$ are the refractive indices of the fiber core and cladding, respectively. Accordingly, the beam divergence of the illumination beam 224 generally depends on the numerical aperture of the fiber 204. Different applications may call for fibers with different numerical apertures, e.g., to provide broad illumination of the full field of view vs. narrow illumination of a selected region of interest within the field of view akin to use of a flashlight. In various examples, instead of switching out optical fibers between applications, the numerical aperture of the optical fiber 204 is adjusted in effect by limiting the angle of incidence at the proximal end with a controllable light source 212, in other words, by changing the numerical aperture associated with the output of the light source. The maximum achievable beam divergence of the illumination beam is, in this case, given by the acceptance angle (corresponding to the inherent numerical aperture) of the fiber 204, which is chosen to be large, and the actual beam divergence is controlled via the effective numerical aperture of the fiber 204 as illuminated by the light source 212.

Figure 3A:
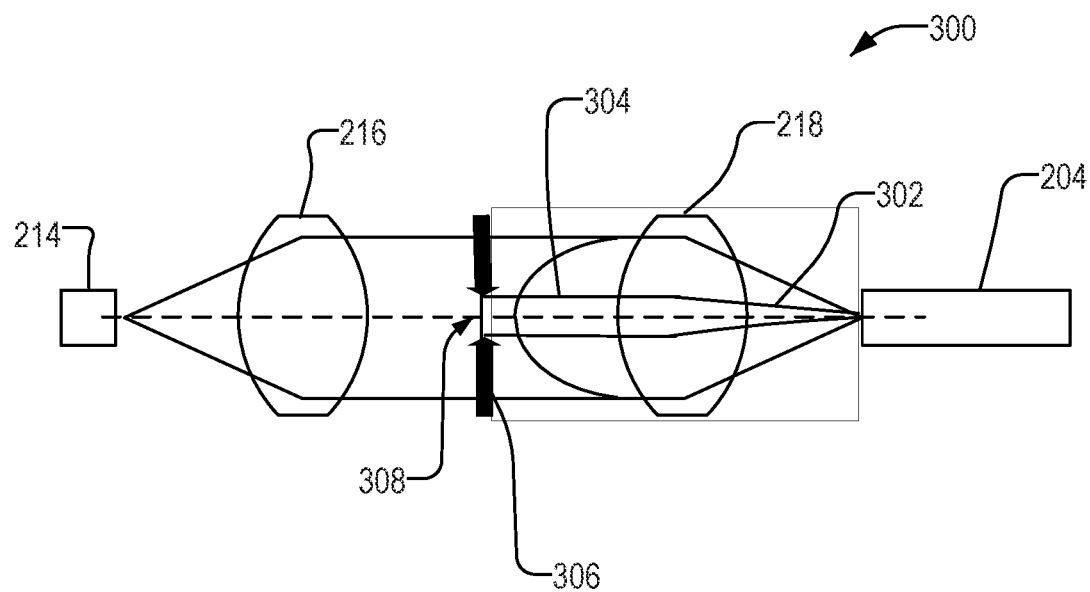
FIGS. 3A and 3B are schematic diagrams of example light sources, as may be used in the system of FIG. 2A, for varying the divergence of the illumination beam.
Figure 3B:
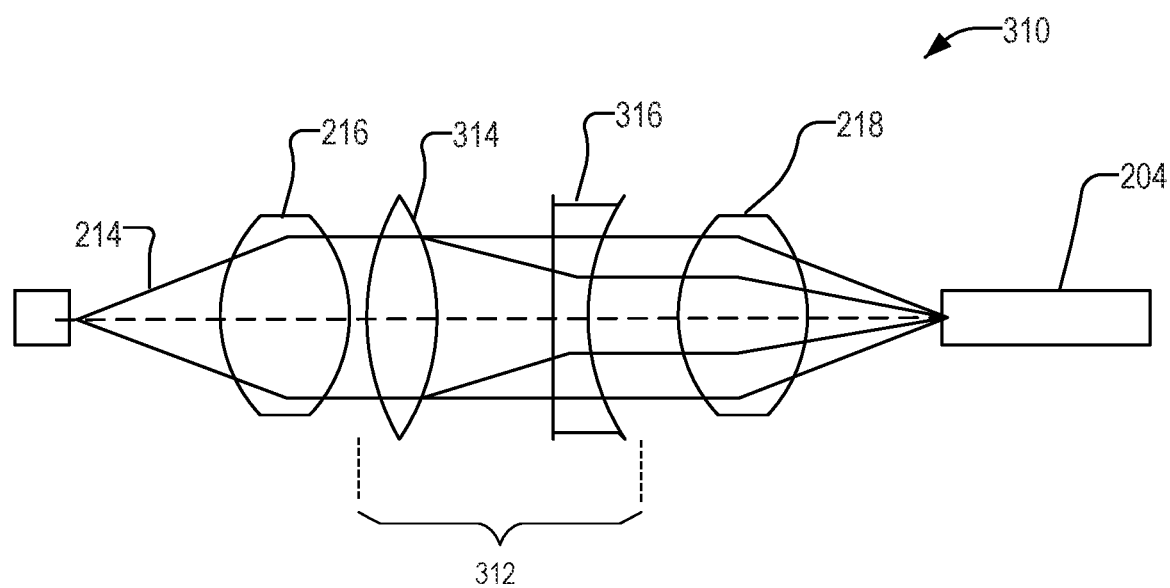

FIGS. 3A and 3B are schematic diagrams of example light sources 300, 310, as may be used in the system 200 of FIG. 2A, for varying the divergence of the illumination beam 224. These light sources 300, 310 are examples of the light source 212, and each include collimating and focusing optics 216, 218 to direct light from one or more light emitters 214 onto the input face of the optical fiber 204. The range of angles, relative to the fiber axis at the proximal end 210, of the incident light 302 is controlled via the width of the collimated beam 304 incident upon the focusing optic 218.

In light source 300 depicted in FIG. 3A, this width is adjustable by a variable beam aperture device 306 placed between the collimating and focusing optics 216, 218. The beam aperture device 306 is configured to block light outside a central, often circular aperture 308 that can be opened and closed to a desired diameter. One example of a beam aperture device 306 is an iris diaphragm, which blocks light with a set of movable thin leaves arranged to define the circular aperture. Other types of beam aperture devices with adjustable aperture sizes may be used.

In light source 310 depicted in FIG. 3B, the width of the collimated beam 304 is adjusted with a beam expander 312. Various types of beam expanders, including telescopic and prismatic beam expanders, may be used. Telescopic beam expanders include refracting or reflective telescopes. The example beam expander 312 depicted in FIG. 3B is a refractive telescope, which includes an objective lens 314 and an image lens 316 separated by the sum of their focal lengths, and achieves a magnification corresponding to the ratio of the focal lengths (which, as depicted, is smaller than 1, corresponding to a reduction in the beam size). More specifically, the depicted beam expander 312 is configured as a Galilean telescope, which uses a positive objective lens 314 and a negative image lens 316 (having an associated negative focal length).

Light sources 300, 310 with beam aperture devices 306 or beam expanders 312 as shown in FIGS. 3A-3B allow changing the divergence of the illumination beam 224 and, thus, the size of the beam spot on the target 226, which may be useful, for instance, to match the illuminated region to a zoom level within the camera images of the target 226.

Figure 4A:
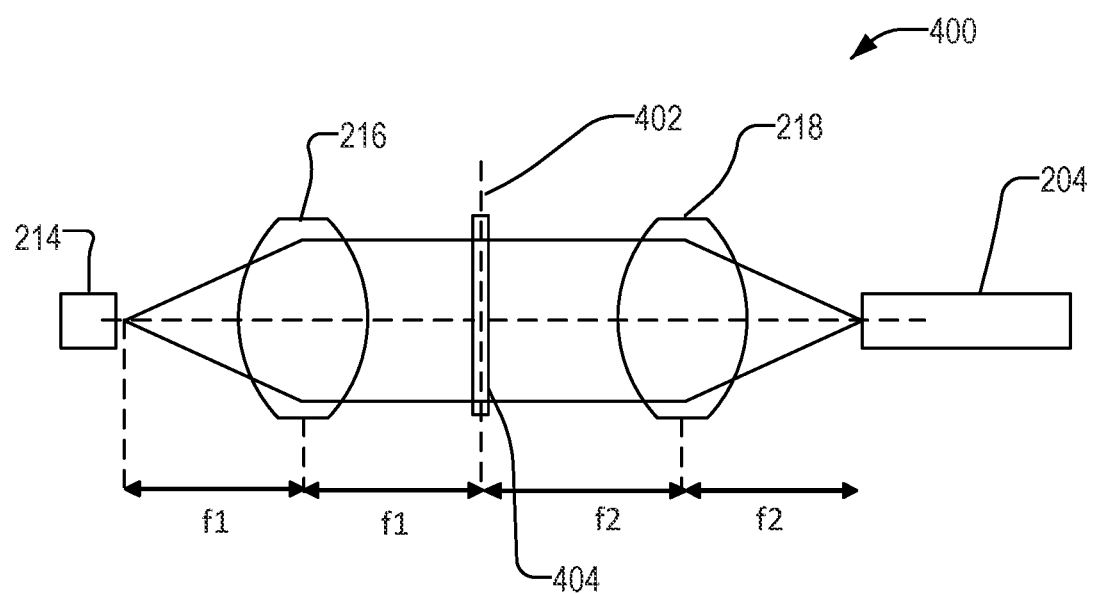
FIGS. 4A-4C are schematic diagrams of example light sources, as may be used in the system of FIG. 2A, for shaping the angular radiant intensity distribution of the illumination beam.
Figure 4B:
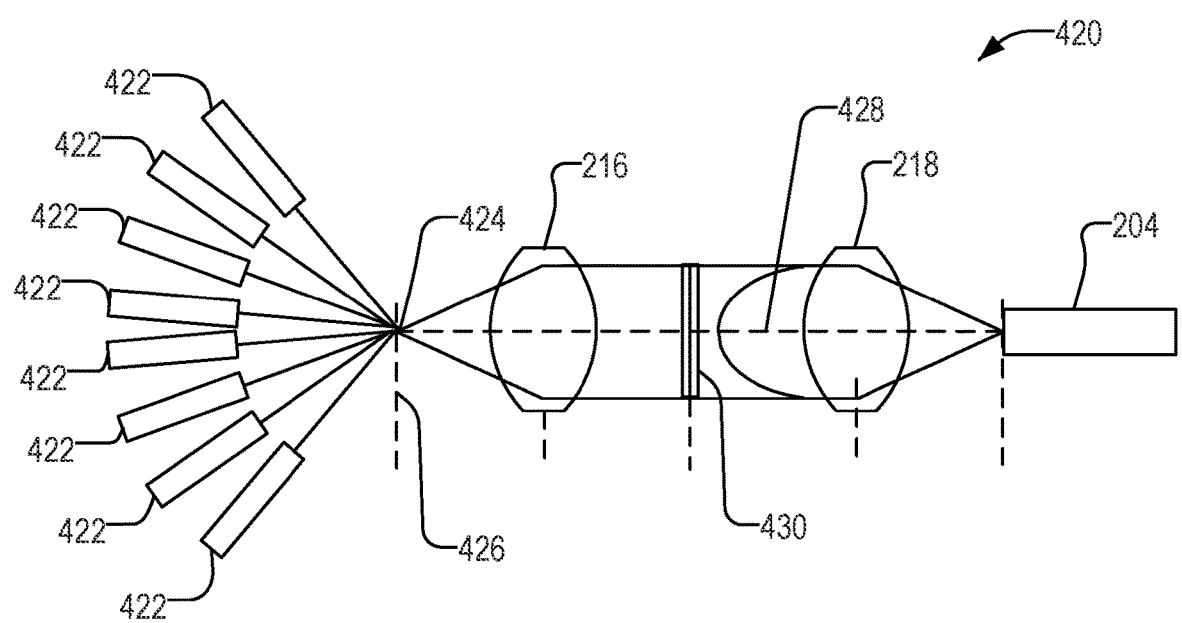
Figure 4C:
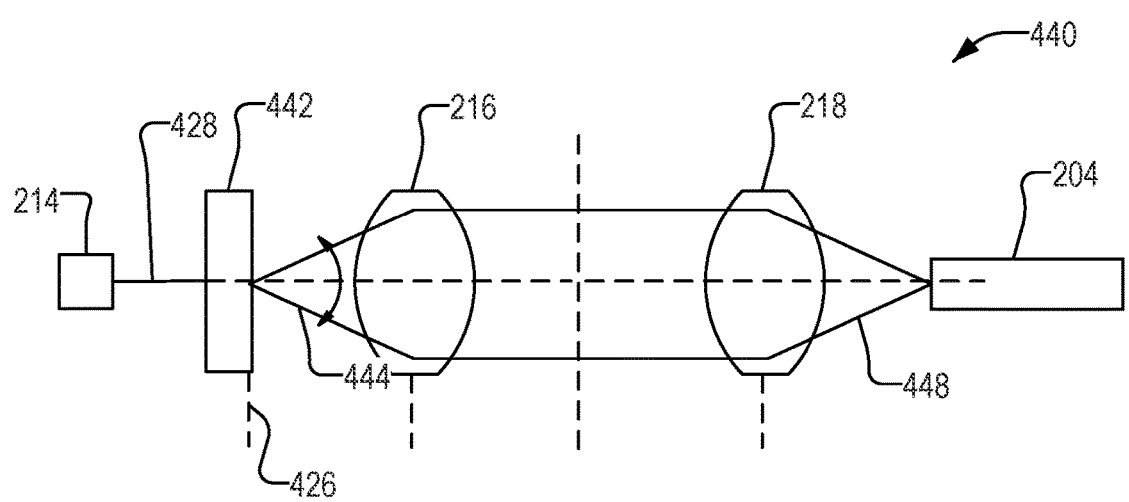

To provide more flexibility in directing the illuminating light where it is desired, light sources in accordance with various examples, described with respect to FIGS. 4A-4C, are configured to allow modifying the angular radiant intensity distribution that is, the intensity as a function of input angle of light coupled into the optical fiber 204 at the proximal end 210. Light coupled into the fiber 204 at a given angle relative to the fiber axis tends to cause a conical light output at the distal end 208 of the fiber, corresponding to an annular (ring-shaped) illumination profile in a plane perpendicular to the direction of propagation of the illumination beam 224. This is the case even if the input light comes from one direction only (rather than being conical itself), and is due to the fact that skew rays, which enter the fiber within a plane that does not include the fiber axis, will hit the core-cladding interface of the fiber at oblique angles and propagate along a generally helical path. For a bent fiber, the path lengths of these helical rays are generally different, which randomizes their output angle, creating a cone of output light. Thus, while light input at 0° (that is, along the fiber axis at the proximal end 210) results in a bright central beam spot at the output, corresponding to an angular radiant intensity distribution that is maximum at 0° (that is, in a direction along the fiber axis at the distal end 208), greater input angles such as, e.g., 15° or 30° result in bright rings, with increasing diameter towards increasing input angle, reflecting a shift in the maximum of the angular radiant intensity distribution at the output to increasing output angles. This relationship can be used to control the angular radiant intensity distribution at the output, corresponding to the radial intensity distribution of the beam spot, via control of the intensity of the input light as a function of input angle. A radially varying intensity distribution across the field of view, in turn, may be used to direct a greater fraction of the total light output by the optical fiber 204 at an area of interest.

FIGS. 4A-4C are schematic diagrams of example light sources 400, 420, 440, as may be used in the system 200 of FIG. 2A, for shaping the angular radiant intensity distribution of the illumination beam 224 via control of the angular intensity distribution of light coupled into the optical fiber 204. The depicted light sources 400, 420, 440 are examples of the light source 212, and each include collimating and focusing optics 216, 218 to direct light from one or more light emitters 214 onto the input face of the optical fiber 204.

The light source 400 of FIG. 4A achieves control over the angular intensity distribution at the fiber input by spatial filtering in a Fourier transform plane 402 between the collimating and focusing optics 216, 218. To elaborate, lenses and other focusing optics effect a physical (as opposed to computational) Fourier transform of incoming light between the spatial and spatial-frequency (or wavevector) domains in that they map parallel light incident upon the optic from different directions (modeled as plane waves with different wavevectors) onto different respective spatial locations in the back focal plane and, conversely, map light coming in from different spatial locations in the front focal plane onto parallel outgoing light propagating in different directions. The light source 400 is configured such that the back focal plane of the collimating optic 216 (which is a plane parallel to the plane of the collimating optic 216 placed at a focal length $f_1$ following the collimating optic 216) coincides with the front focal plane of the focusing optic 218 (which is a plane parallel to the plane of the focusing optic 218 placed at the focal length $f_2$ preceding the focusing optic 218). The spatial intensity distribution in that plane is the Fourier transform of the spatial-frequency distribution at the front focal plane of the collimating optic 216 as well as of the back focal plane of the focusing optic 218, and thus constitutes the Fourier transform plane 402. By controlling the spatial intensity distribution of the light in the Fourier transform plane 402, the angular distribution of light incident upon the optical fiber 204 can be controlled.

To facilitate control over the spatial intensity distribution in the Fourier transform plane 402, the light source 400 may include, in that plane 402, a programmable spatial filter 404 made from a material that is controllably transmissive in the applicable wavelength range (e.g., the visible and/or infrared regime). The programmable spatial filter 404 may, for example, include a liquid crystal material disposed between two optically transmissive plates, and electrically conductive and optically (or UV) transmissive layers (e.g., of indium tin oxide) disposed on the plates that are structured to form electrodes creating multiple individually addressable regions (or pixels) within the liquid crystal layer. The transmissivity of the liquid crystal in these regions can be adjusted via application of an electrical voltage across the liquid crystal layer in each region. The programmable spatial filter 404, thus, includes multiple variably transmissive and individually controllable elements, along with electronic circuitry for addressing these elements. In some examples, these elements form annular regions about the optical axis of the collimating and focusing optics 216, 218, each associated with a different range of illumination angles.

FIG. 4B illustrates an alternative light source 420, which utilizes multiple light emitters 422 that direct their outputs at a focal region 424 in the front focal plane 426 of the collimating optic 216 from multiple angles relative to the optical axis 428. The collimated light is refocused, by the focusing optic 218, onto the input of the optical fiber 204, at different input angles for light coming from different emitters 422. If the focal lengths of the collimating and focusing optics 216, 218 are equal, the input angle relative to the optical axis 428 for each light emitter 422 equals the respective angle of light emission relative to the optical axis 428. If the focal lengths differ, the tangent of each input angle equals the tangent of the respective angle of light emission, multiplied by the ratio of the focal lengths of the collimating and focusing optics 216, 218. Thus, by controlling the relative intensity of the emitters 422 as a function of their respective angles relative to the optical axis 428, the angular intensity distribution at the input of the optical fiber 204 can be directly controlled. This approach can also be used in a modified light source that omits the collimating and focusing optics, and instead directs the light directly from multiple emitters at the fiber input. The use of collimating and focusing optics 216, 218 is beneficial if local interference between light from multiple emitters causes a laser speckle pattern, since such laser speckle can be diminished with a laser speckle reducer 430 placed at the Fourier transform plane 402 between the collimating and focusing optics 216, 218.

FIG. 4C illustrates yet another alternative light source 440, in which the angular intensity distribution of light coupled into the optical fiber 204 is controlled by scanning light from one or more light emitters 214 across the collimating optic 216 as the intensity is varied, in accordance with various examples. As shown, (optionally collimated) light coming from the light emitter(s) 214, as it propagates along the optical axis 428, is intercepted by a beam sweeper 442 placed at the front focal plane 426 of the collimating optic 216. The beam sweeper 442 changes the direction of propagation of the light as a function of time, thereby scanning a light beam 444 exiting the beam sweeper 442 across the surface of the collimating optic 216. The angle relative to the optical axis 428 at which the beam 444 enters the collimating optic 216, herein also the "scanning angle," will result in the same angle relative to the optical axis 428 of the beam 448 exiting the focusing optic 218 if the focusing lengths of the collimating and focusing optics 216, 218 are the same. In this manner, the light beam 448 coupled into the optical fiber 204 can be scanned across a range of input angles by scanning the light beam 444 entering the collimating optic 216 across that same range of angles.

The beam sweeper 442 may be implemented by any of various devices known to those of skill in the art. In some examples, one or more acousto-optic modulators are used. Acousto-optic modulators use the acousto-optic effect to diffract light using acoustic waves generated, for example, by a piezoelectric transducer attached to a plate made of glass or some other material transparent to light. The diffraction angle depends on the frequency of the acoustic waves, and the amount of light diffracted at that angle depends on the intensity of the acoustic. Thus, using an acousto-optic modulator as the beam sweeper 442, the diffraction angle, which corresponds to scanning angle between the beam 444 and the optical axis 428, and the intensity of the beam 444 can be adjusted in a coordinated fashion by simultaneously controlling the acoustic frequency and intensity, e.g., via the frequency and amplitude of vibrations generated by the piezoelectric transducer. A single acousto-optic modulator allows scanning the beam 444 along one dimension. To achieve two-dimensional scanning, two crossed acousto-optic modulators may be used. Since the optical fiber 204 itself tends to create an annular output even if light enters the fiber 204 from only one direction, a scan along a line across the surface of the collimating optic 216, intersecting the optical axis 428, may suffice in many cases. Further, the scan may be limited to a line segment between normal incidence onto the collimating optic and a maximum desired input angle.

In an alternative example, one or more electrically driven rotating mirrors (e.g., as known from mirror galvanometers) may serve as the beam sweeper 442 to deflect incoming light at an electrically controllable angle. As with acousto-optic modulators, a single rotating mirror allows scanning the beam along one transverse direction, whereas two crossed rotating mirrors achieve full scanning flexibility in both transverse directions. Unlike acousto-optic modulators, however, rotating mirrors do not themselves modify the intensity of the light. Therefore, when a using rotating mirror, or any other kind of beam sweeper 442 that changes merely the angle of the light relative to the optical axis 428, the output intensity of the light emitters may be varied (directly, or indirectly via an amplitude modulator at the emitter output) in synchronization with the scanning angle to effect the desired angular intensity distribution of light coupled into the optical fiber 204. For example, the system controller and data processor 122, or a separate controller, may simultaneously control the light emitter(s) 214 (or associated amplitude modulators) and the beam sweeper 442 in accordance with a desired functional dependence (e.g., cosine) between intensity and angle, as may be stored in memory of the system controller and data processor 122. Alternatively, the light emitter(s) 214 may be controlled based on a signal received from the beam sweeper 442 and/or vice versa, or both light emitters 214 and beam sweeper 442 may execute predetermined (e.g., linear or sinusoidal) sweeps of the light intensity and angle, respectively, with trigger signals serving to synchronize the sweeps.

With a beam sweeper 442, an arbitrary intensity distribution across the target at the resolution of the beam spot can be created by (repeatedly) scanning the illumination beam 224 across the target, and simultaneously tuning the beam intensity, at a scan rate that is at least equal to, and coordinated with, the image acquisition rate of the camera(s), such that each image acquired by the camera sensor(s) aggregates light received over a full scan period or an integer multiple of the scan period (understood to be the period of a full scan in one direction). In various examples, image acquisition rates are between 30 frames per second and 120 frames per second, and scan repetition rates are between 300 Hz and 12 kHz. With scanning illumination, a full-frame readout of the camera sensor(s) will preferably be used. A shutter may prevent light from reaching the sensor(s) during read-out, as well as, in cases where multiple successive scans are performed between readouts to accumulate enough photons, during periods in which the beam sweeper 442 is set back to the starting position. The system controller and data processor 122 may control the operation of the light emitter(s) 214, beam sweeper 442, camera sensors, and shutter(s) simultaneously and in a coordinated manner.

The divergence or shape of the illumination beam 224, instead of being controlled indirectly via the distribution of light coupled into the fiber 106, 204 at the proximal end 210, may alternatively be adjusted directly by a controllable illumination beam source 104 at the distal end of the illumination device 102, 202. For this purpose, the optical fiber 106, 204 may be equipped, at its output, with controllable optical and/or mechanical component, which together with the distal fiber end 208 constitute the controllable illumination beam source 104. While such added hardware at the distal fiber end may increase the diameter of the illumination device 102, 202, it can, in some examples, provide greater flexibility in shaping the illumination beam 224 than the light source 108, 212 at the proximal end 210, and can further allow changing the direction of the illumination beam 224. Note that, in systems where a camera is integrated with the illumination device, the added optical components for modifying the beam at the distal fiber end may be positioned such that they affect only the beam, but do not interfere with the camera optics. For example, if the illumination beam source includes two fiber bundles on opposite sides of a camera or cameras, as shown in FIG. 2B, the added optical components may be duplicated to separately affect the light emanating from the two fiber bundles.

FIGS. 5A-5E are schematic diagrams of example illumination devices, as may be used in the system 200 of FIG. 2A, with controllable illumination beam sources (constituting examples of illumination beam source 104) for manipulating the beam divergence, shape, and/or direction of the illumination beam 224.

Figure 5A:
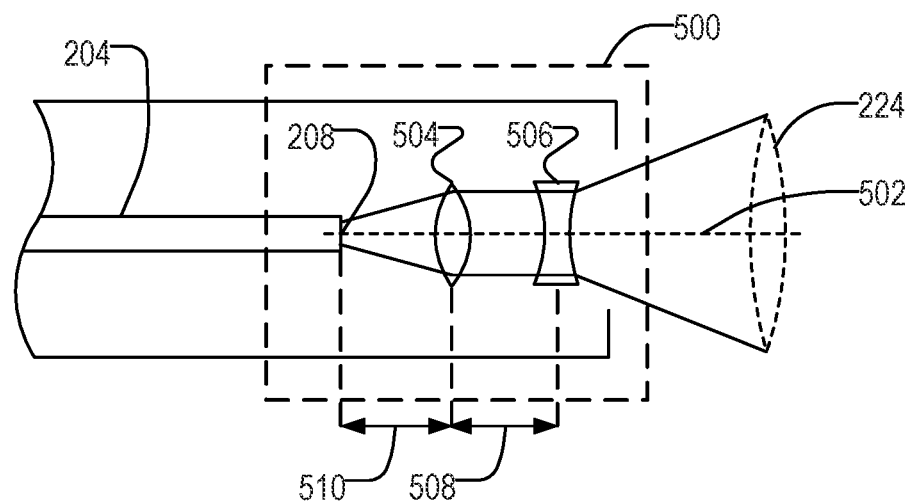
FIGS. 5A-5E are schematic diagrams of example illumination devices with controllable illumination beam sources, as may be used in the system of FIG. 2A, for manipulating the beam divergence, shape, and/or direction of the illumination beam.

FIG. 5A shows an illumination beam source 500 that uses an adjustable lens system at the output of the optical fiber 204 to vary the illumination beam divergence. The lens system may generally include one or more lenses arranged movably along the optical axis 502 defined by the fiber 204 at its distal end 208 (along which the illumination beam 224 leaving the distal end 208 propagates). For example, as illustrated, the lens system may include a positive (e.g., convex) lens 504 for refocusing the diverging beam output by the optical fiber 204 and a negative (e.g., concave) lens 506 for further increasing the beam divergence, with a variable distance 508 between the two, and optionally a variable distance 510 of the lens system from the distal fiber end 208, to adjust the overall focal length of the lens system and the resulting divergence of the illumination beam 224. Alternatively, a single lens at a variable distance from the distal fiber end may be used to adjust the illumination beam divergence. The lenses (e.g., 504, 506) of the lens system may be moved by electrically controlled micromechanical actuators, such as, for example, piezoelectric actuators or microelectromechanical systems (MEMS), which receive electrical control signals from the illumination controller 120, e.g., via wires running in the illumination device 102, 202 alongside the optical fiber 204, or via wireless transmission from a transmitter associated with the controller 120 to a receiver associated with the illumination beam source 500.

Figure 5B:
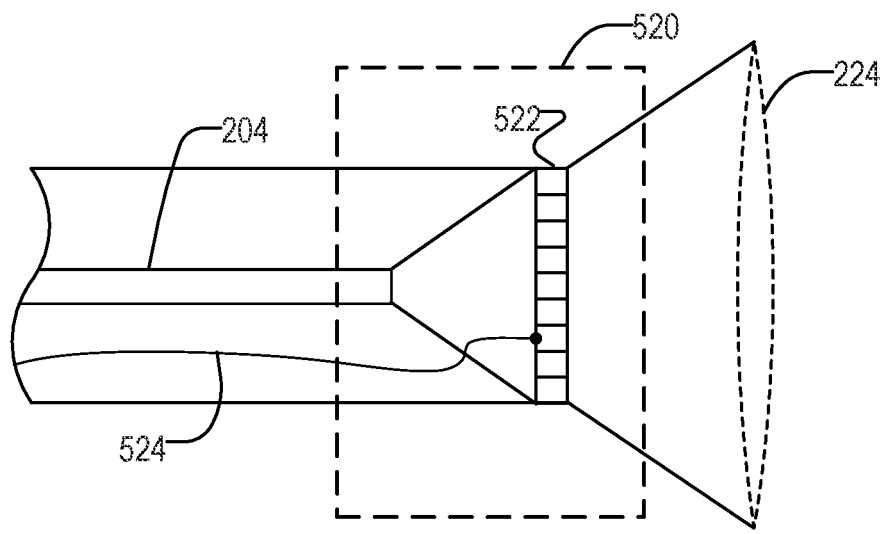

FIG. 5B shows an illumination beam source 520 including a programmable spatial filter 522 at the fiber output to control the beam divergence or, more generally, the beam shape. The programmable spatial filter 522 may include, across the area of the filter, multiple individually addressable regions of controllable transmissivity or refractive index. For example, the programmable spatial filter 522 may be implemented with a liquid-crystal-based transmissivity filter as described with reference to FIG. 4A above, except smaller in dimensions to fit within the illumination device 102, 202. The optical properties (e.g., transmissivity or refractive index) of the filter regions can be set with electrical control signals transmitted from the illumination controller 120 via electrical wires 524 or wirelessly.

Figure 5C:
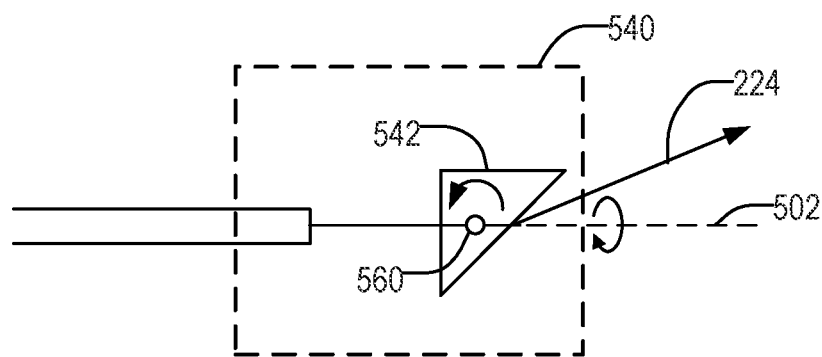
Figure 5D:
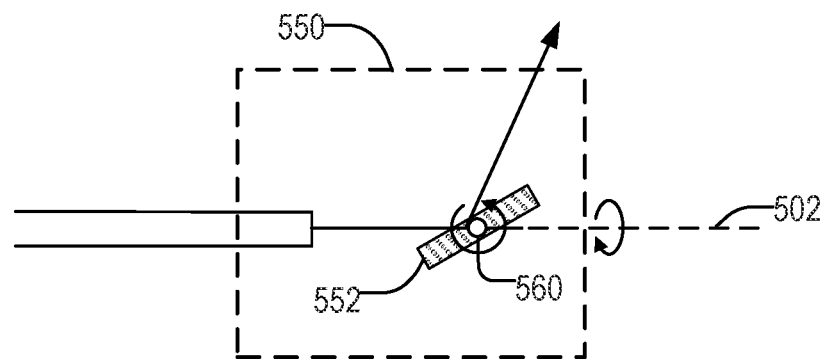
Figure 5E:
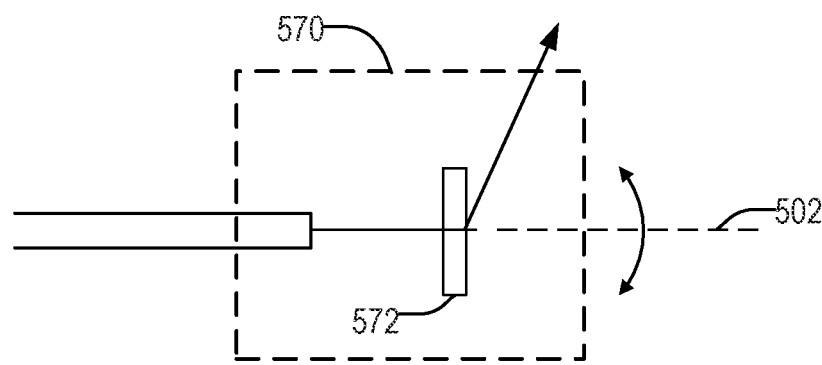

FIGS. 5C-5E illustrate examples of illumination beam sources that include movable or otherwise adjustable refractive, reflective, or diffractive optics at the distal fiber end 208 that control the direction of the illumination beam 224—in other words, that function as beam sweepers. In FIG. 5C, the illumination beam source 540 includes an optical wedge 542 at the fiber output that refracts the illumination beam 224 (which initially propagates along the optical axis 502) away from the optical axis 502. Similarly, in FIG. 5D, the illumination beam source 550 includes a mirror 552 that reflects the illumination beam 224 away from the optical axis 502. The wedge 542 or mirror 552 may be rotatable about an axis of rotation 560 perpendicular to the optical axis 502 to change, via the tilt angle of the wedge 542 or mirror 552, the angle relative to the optical axis 502 at which the diffracted or reflected illumination beam 224 propagates. Further, the wedge 542 or mirror 552 may be rotatable about the optical axis 502 to move the illumination beam 224 (or, more precisely, the central beam axis) at a fixed angle relative to the axis 502 along a cone, and thus the illumination beam spot on the target 226 along a circle centered at the intersection of the optical axis 502 with the target 226. Collectively, the rotational positions (or angles) of the wedge 542 or mirror 552 about the two axes 560, 502 provide two degrees of freedom to direct the illumination beam 224 at a desired location in two dimensions on the target 226. The rotational positions may be changed by piezoelectric actuators, MEMS, or other electrically controlled micromechanical actuators, controlled remotely by the illumination controller 120 via wires or wirelessty. As will be readily apparent to those of ordinary skill in the art, in lieu of the wedge 542 or mirror 552, other rotatable or generally movable optical components may be used to change the illumination beam direction by refraction, reflection, or diffraction.

FIG. SE shows an illumination beam source 570 including one or more acousto-optic modulators 572 at the fiber output for controlling the direction of the illumination beam 224. As described above with reference to FIG. 4C, acousto-optic modulators use acoustic waves traveling across a transparent plate to diffract light at a diffraction angle that depends on the frequency of the acoustic waves and in an amount that depends on their intensity. A pair of crossed acousto-optic, modulators can be used to cause diffraction in two dimensions. The acoustic waves can be generated, e.g., by a piezoelectric transducer, which may operate in response to control signals received from the illumination controller 120. The acousto-optic modulator(s) 572 allows scanning the illumination beam 224 across the target 226, and if the acoustic intensity is controlled in synchronization with the acoustic frequency, the beam intensity can be varied as the beam spot on the target 226 moves.

The foregoing examples achieve spatial control over the illumination of the target 226 with a single illumination beam 224, generated at the output of an optical fiber or fiber bundle 204 (or multiple closely spaced and jointly addressed fiber bundles), that is manipulated by suitable optical elements in the light source 108 at the input or in the illumination beam source 104 at the output of the optical fiber 204. In the following examples, the illumination beam 224 is composed of multiple "microbeams" generated by separate respective individually addressable optical fibers or fiber bundles (herein also referred to as individually addressable "sets of optical fibers") of generally lower numerical aperture than used for a single beam 224. Spatial illumination control is achieved, in this case, by turning the microbeams individually on or off, or setting their relative intensities and optionally their directions.

Figure 6A:
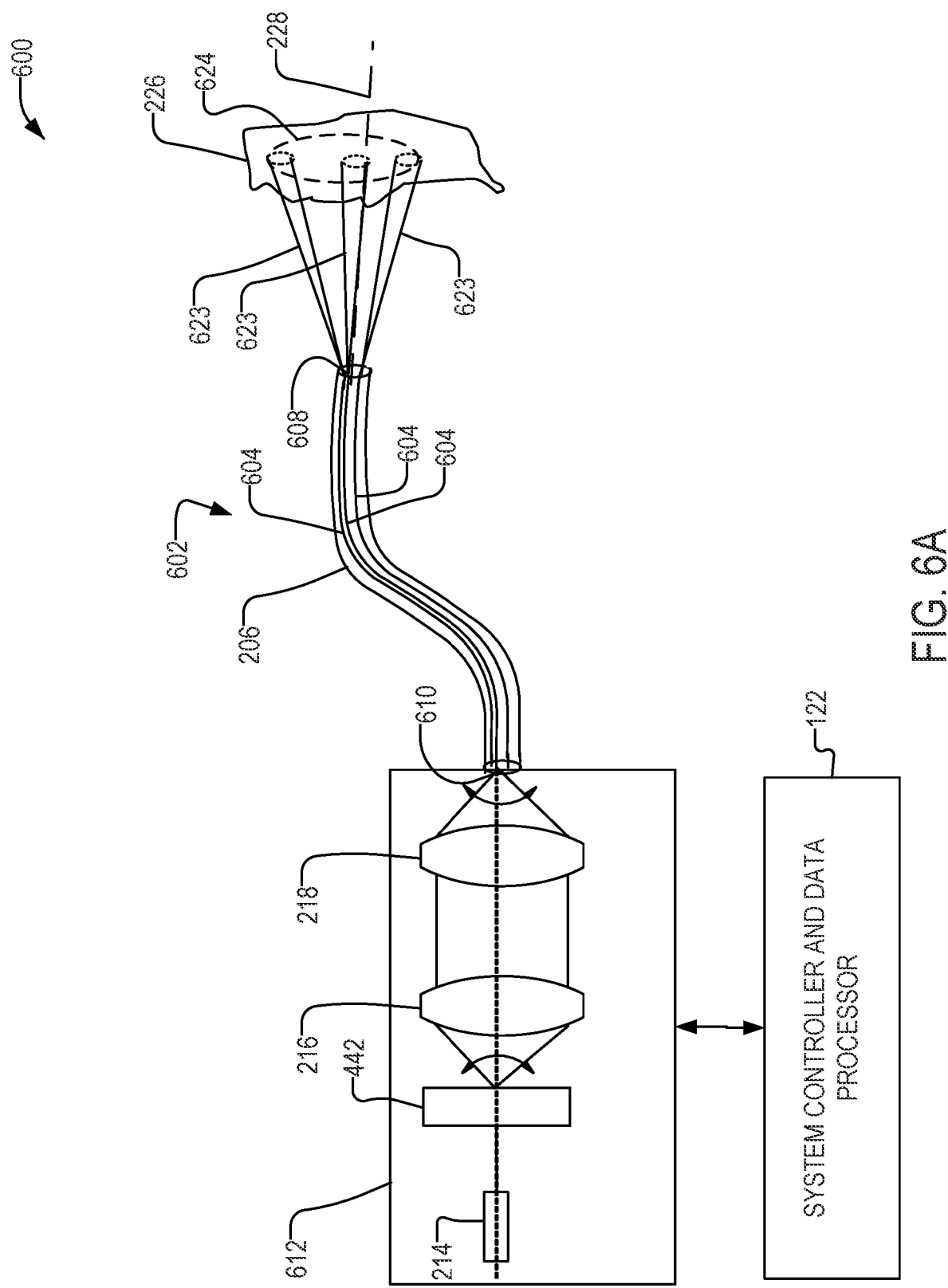
FIG. 6A is a schematic diagram of an example fiber-optic illumination system with multiple individually addressable fiber bundles.
Figure 6B:
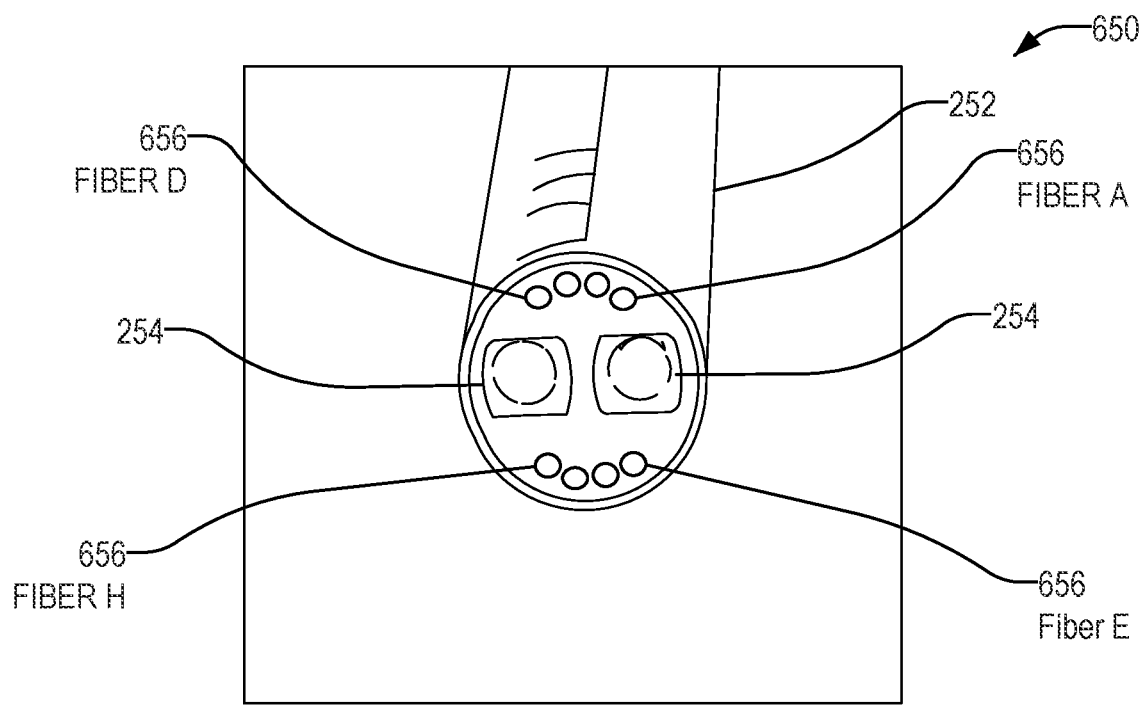
FIG. 6B is a front schematic view of the distal end of an example endoscope as may be used in the system of FIG. 6A.

FIG. 6A is a schematic diagram of an example fiber-optic illumination system 600 with multiple individually addressable fiber bundles. The system 600 includes an illumination device 602 including the individually addressable fiber bundles (or, more generally, sets of one or more fibers) 604 housed in a rigid or flexible tube 206, and a light source 612 that couples light into the fiber bundles 604 at their proximal end(s) 610 (which can, for practical purposes, be assumed to be all collocated, although the possibility of different fiber bundles 604 ending in different locations is not excluded in principle). Like in the system 200 of FIG. 2A, the illumination device 602 may be integrated with or more cameras, placed at or near the distal end of the device 602, into an endoscope. The system 600 further includes a system controller and data processor 122, which may include illumination and camera controllers 120, 114, an image processor 116, and/or a user interface 118, to operate the endoscope and associated light source 612.

The different fiber bundles 604 may be configured, as conceptually shown, to emit microbeams 623 in different directions to illuminate different respective regions on the target 226. While three microbeams 623 are shown in FIG. 6A, it will be understood that, in general, any number of two or more separate fiber bundles 604 and associated microbeams 623 may be used. The individual fiber bundles 604 may be chosen to have a lower numerical aperture than the fiber (bundle) 204 in system 200, and therefore generate narrower (lower-divergence) beams 623 (hence called "microbeams"). Collectively, the microbeams 623 may form an illumination beam 624 that illuminates a larger area on the target 226. The cross-sectional intensity distribution of that overall illumination beam 624 can be varied via the selection or relative intensities of the microbeams 623.

To facilitate individually addressing the fiber bundles 604, the relative positions of the fiber bundles 604 at their distal end(s) 608 map in a deterministic fashion onto respective relative positions at the proximal end(s) 610. The light source 612 is configured to facilitate coupling light selectively into any one (or more) of the fiber bundles 604. For instance, as shown, the light source 612 may include a beam sweeper 442 (e.g., as shown in FIG. 4C) preceding the collimating optic 216, e.g., implemented by an acousto-optic modulator, to allow directing the beam of the light source at a given point at the input of the illumination device 602, and thus on a selected fiber bundle 604. For example, one microbeam 623 may be turned on at a given time. An overall intensity distribution composed of the illumination spots of multiple microbeams 623 can nonetheless be achieved if the light source 612 scans the input across corresponding fiber bundles 604 within the acquisition time of the camera(s) for a single frame. In addition to changing the location of the light spot on the target 226, this approach also allows simultaneously changing the illumination intensity via the optical power output by the light source 612. Alternatively to scanning light, the light source 612 may include a programmable spatial filter 404 between the collimating and focusing optics 216, 218, e.g., as shown in FIG. 4A, to shape the focused beam that launches light in the fiber bundles 604, which may allow addressing multiple fiber bundles 604 simultaneously. Yet another option is to use multiple light emitters to direct input light onto different respective fiber bundles 604, optionally with different optical power.

Instead of using the light source 612 to selectively generate and set the intensities of the microbeams 623, the system 600 can also, in some examples, equip the illumination beam source 104 with optical elements that provide this functionality. For example, the illumination beam source 104 may employ adjustable light attenuators, e.g., implemented by liquid-crystal transmissive attenuators, at the distal end 608 of each individual fiber bundle 604 to tune the intensity of each microbeam 623 before it reaches the target 226. In another example, shutters associated with fiber bundles may be used to turn the microbeams 623 on or off.

FIG. 6B is a front schematic view of the distal end of an example endoscope 650, as may be used in the system of FIG. 6A, with multiple individually addressable fiber bundles 656. The endoscope 650 is configured similarly to that of FIG. 2B, with two cameras 254 placed side by side, and optical fiber placed in the surrounding tube 252 above and below the cameras 254. Instead of forming two fiber bundles 256 that are operated jointly, however, the endoscope 650 may include two sets of four individually addressable, lower-numerical-aperture fiber bundles 656 arranged in an arc (labeled A-D and E-H, respectively), which allow creating eight separate microbeams 623. The fiber bundles 656 may be arranged in a similar fashion at the proximal end of the endoscope 650 for straightforward mapping between pairs of a fiber input and a fiber output belonging to the same fiber bundle. The multiple microbeams 623 need not come at the cost of increased size of the endoscope 650; the endoscope 650, like the endoscope 250 of FIG. 6A, may, for example, have a tube diameter of approximately 8.8 mm or approximately 12 mm.

Figure 6C:
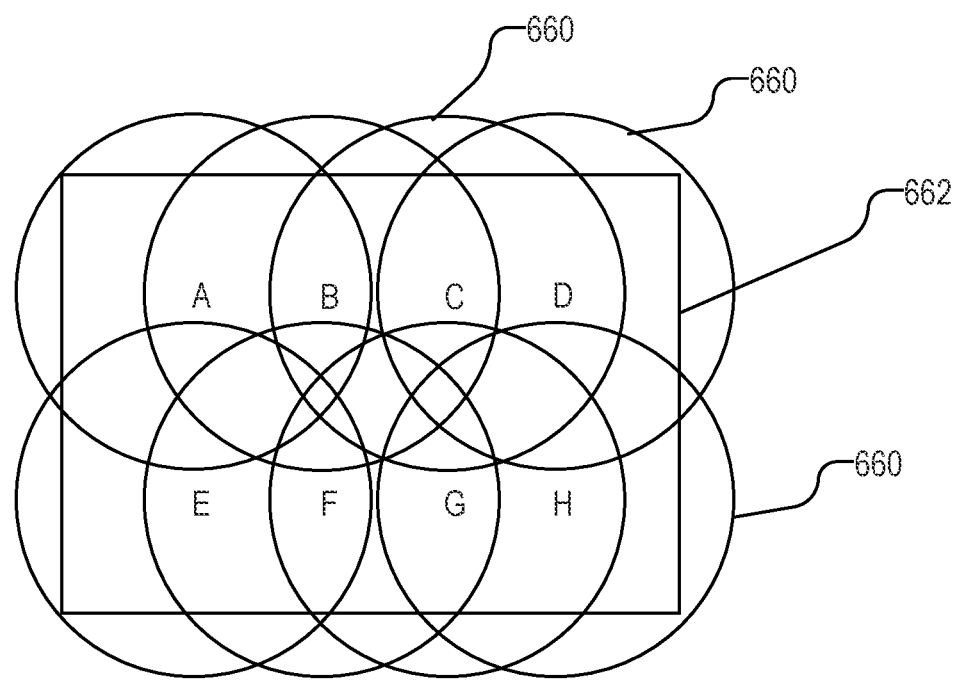
FIG. 6C is a schematic view of an example of illumination achieved with the endoscope of FIG. 6B.

FIG. 6C is a schematic view of the illumination achieved with the endoscope 650 of FIG. 6B. As illustrated by circular outlines, each of the fiber bundles 656 may generate its own respective beam spot 660 within the field of view 662 of the cameras 254. The microbeams 623 and associated beam spots 660 substantially overlap, resulting in coverage of the entire field of view 662, with a brightly illuminated area in the middle of the field of view 662 and lower levels of illumination along the periphery of the field of view 662 when all microbeams 623 are turned on simultaneously. While the beam spots 660 are depicted as uniform in intensity, they may in reality have an intensity distribution characterized by a gradual, e.g., radially symmetric Gaussian, fall-off from a peak intensity at the center; the circular outline may be defined, in practice, by a fall-off to, e.g., 1/e of the peak intensity. The overall illumination from all microbeams 623 together may, as a consequence, be more uniform than depicted. On the other hand, when only one or a subset of the microbeams 623 are turned on, illumination is confined to a corresponding sub-region of the field of view 662. As will be readily appreciated, the spatial resolution of such illumination control generally increases with the number of individually addressable fiber bundles 604, as well as the ability, if any, to adjust the individual microbeams 623 themselves (e.g., in their divergence, direction, and/or intensity). Although FIGS. 6B and 6C show eight fiber bundles 656 and eight beam spots 660, an endoscope (e.g., endoscope 650)) may include any number of fiber bundles and corresponding beam spots. Moreover, the fiber bundles may be arranged at the distal end (and proximal end) in any arrangement, including the arc shapes shown in FIG. 6B.

Figure 7A:
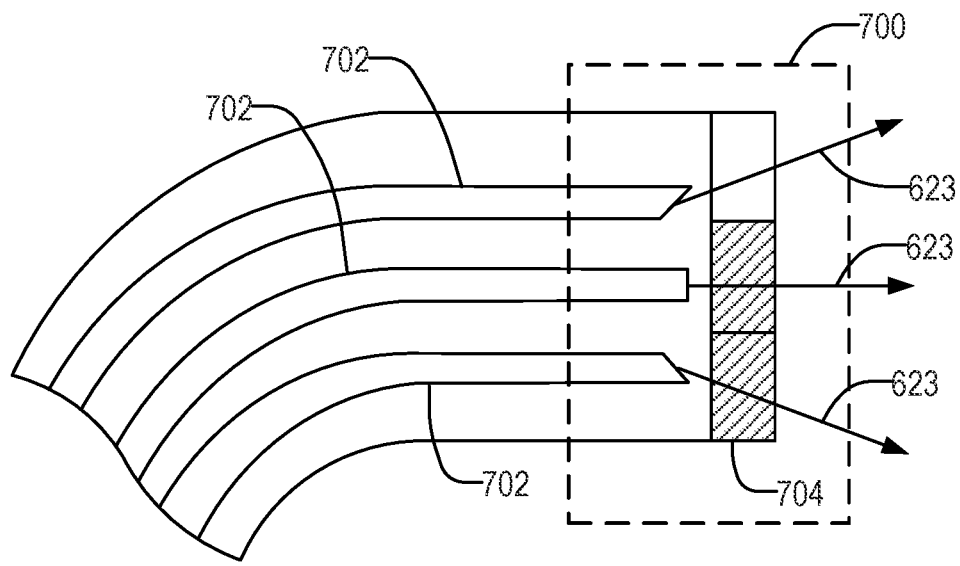
FIGS. 7A and 7B are schematic diagrams of example illumination devices with multiple individually addressable fiber bundles, as may be used in the system of FIG. 6A.

FIGS. 7A and B are schematic diagrams of example illumination devices 700, 750 with multiple individually addressable sets of optical fibers, as may be used in the system 600 of FIG. 6A. FIG. 7A shows an illumination beam source 700 at the distal end of the illumination device, applicable both to examples in which each individually addressable set of fibers includes only one large-core optical fiber and examples in which each individually addressable set of fibers is itself a bundle of fibers (constituting a sub-bundle of the bundle formed by the entirety of sets of fibers). The individual fibers 702 are oriented in parallel at the distal end, but cleaved at different angles relative to the optical axis, such that the differently oriented output faces of the fibers 702 generate microbeams in different directions. Optionally, the illumination beam source may also include a variable pixelated transmissive attenuator 704 that allows tuning the transmitted intensity of each microbeam separately from the other microbeams.

Figure 7B:
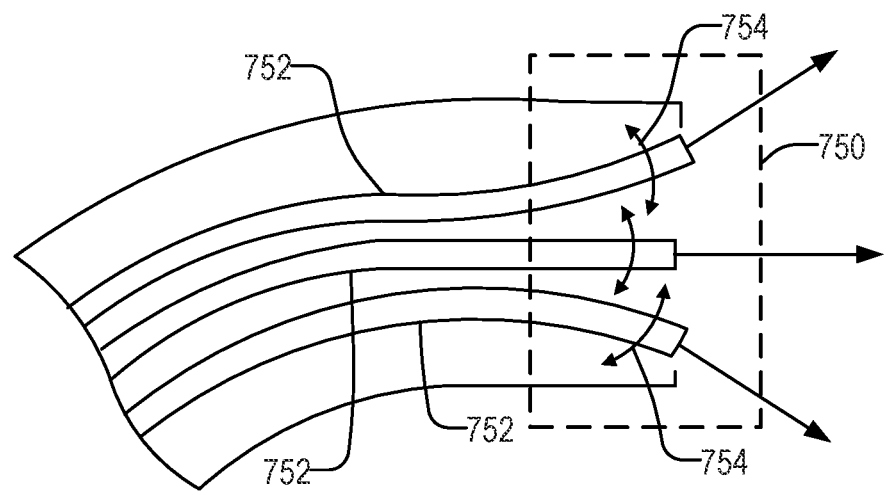

FIG. 7B shows an alternative illumination beam source 750, in which different sets of optical fibers 752 (e.g., fibers or fiber bundles) are oriented with their fiber (bundle) axes in different directions at their distal ends to achieve the microbeams in different directions. In some examples, the orientations of the distal fiber ends are fixed, and control over the illuminated regions within the field of view is achieved, accordingly, via the selection of the fiber sets 752 that are turned on. In other examples, as indicated by the arrow 754, the physical fiber ends are movable, e.g., with piezoelectric or MEMS actuators, allowing the directions of individual microbeams to be altered via the orientations of the distal fiber ends, which provides further flexibility for illumination.

Figure 8:
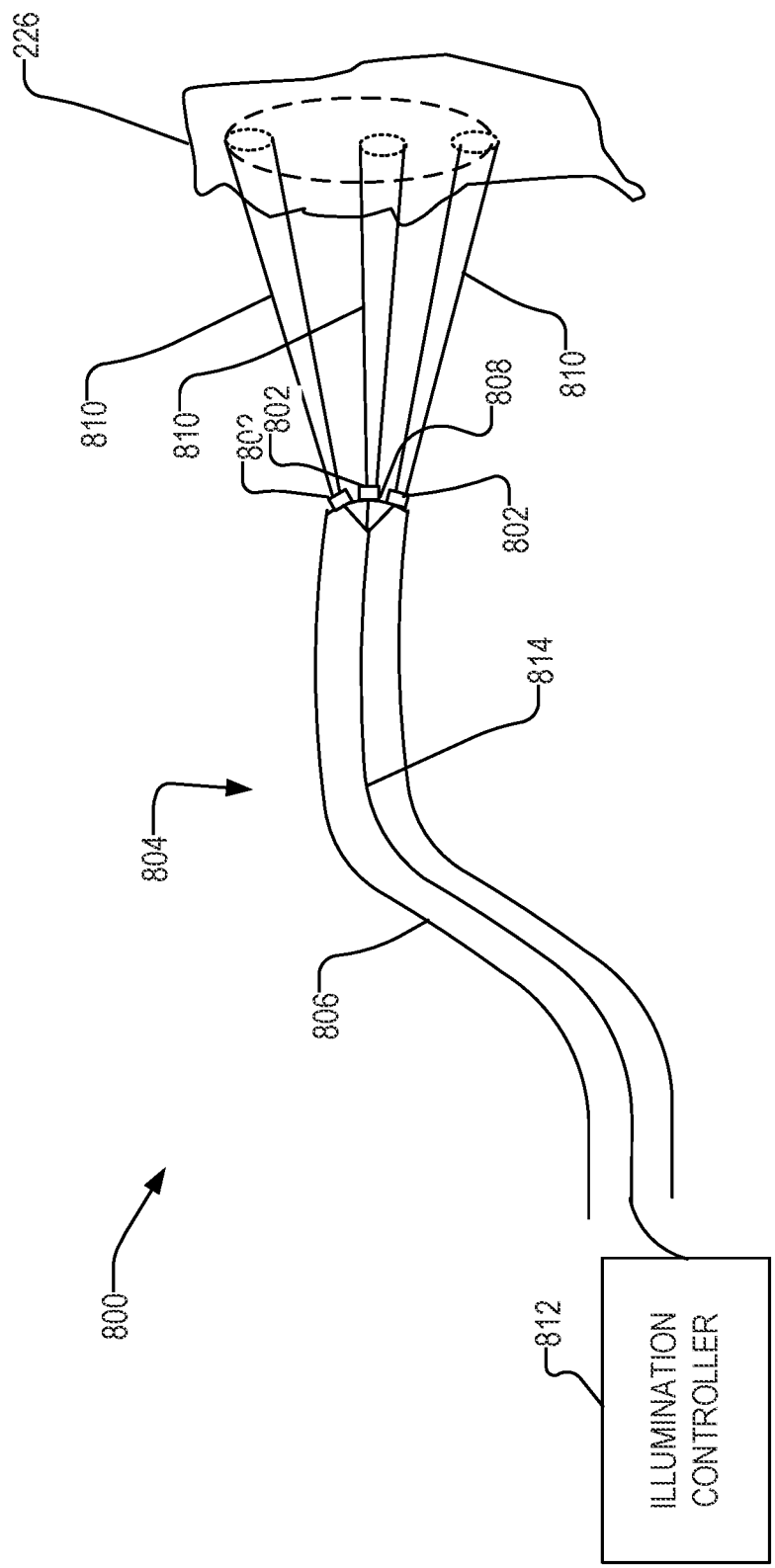
FIG. 8 is a schematic diagram of an example illumination system including multiple light emitters at a distal end of an illumination device.

FIG. 8 is a schematic diagram of an example illumination system 800 including multiple light emitters 802 at a distal end of an illumination device 804. The illumination device 804 includes a solid or hollow shaft 806, whose distal end is, in use, positioned near the target 226. The emitters 802, which may be, for example, LEDs or lasers, are mounted at the distal end 808 of the shaft 806, and are configured and oriented to emit microbeams 810 with narrow transmission angles (e.g., less than 20°) into different directions, allowing the direction of the illumination to be varied by selectively operating the emitters 802. If multiple emitters 802 are turned on simultaneously, their microbeams 810 may collectively form an illumination beam that may illuminate multiple discrete regions or a larger contiguous region on the target 226, and whose intensity distribution can be varied via the light outputs of the individual emitters 802. The emitters 802 may be powered and controlled by an external illumination controller 812 (an example of the illumination controller 120) via electrical wires 814; with a hollow shaft 806, the wires 814 may run through the shaft 806. The system 800 may further include one or more cameras, which may be integrated with the illumination device 804 at or near the distal end 808 of the shaft 806 to collectively form an endoscope. The emitters 802 may be arranged, for instance, in rows above and below the cameras like the optical fiber bundles shown in FIG. 6B. Alternatively, if space permits, the emitters 802 may form a ring surrounding the cameras, Various other configurations are also possible.

Various approaches to spatially controlling the illumination of the target 226 via control over the beam divergence, shape, and/or direction of the illumination beam 224, which, in some examples, may be composed of multiple controllable microbeams 623, 810, have been described. As will be readily appreciated by those of ordinary skill in the art, multiple approaches may be used in combination. For example, control over the illumination beam divergence by limiting the input angles at the proximal end of a fiber-optic illumination device may be combined with control over the direction of the illumination beam at the fiber output with an acousto-optic modulator. As another example, in devices with multiple individually addressable sets of optical fibers or light emitters, control over the overall illumination beam via relative intensities of its constituent microbeams can be augmented by control over the beam divergence, shape, or direction of the microbeams themselves, e.g., as achieved by the light source coupling light sequentially into individual fibers or with adjustable optical elements (e.g., adjustable focal-length lens systems, rotatable mirrors, etc.) placed in the paths of the microbeams.

Figure 9:
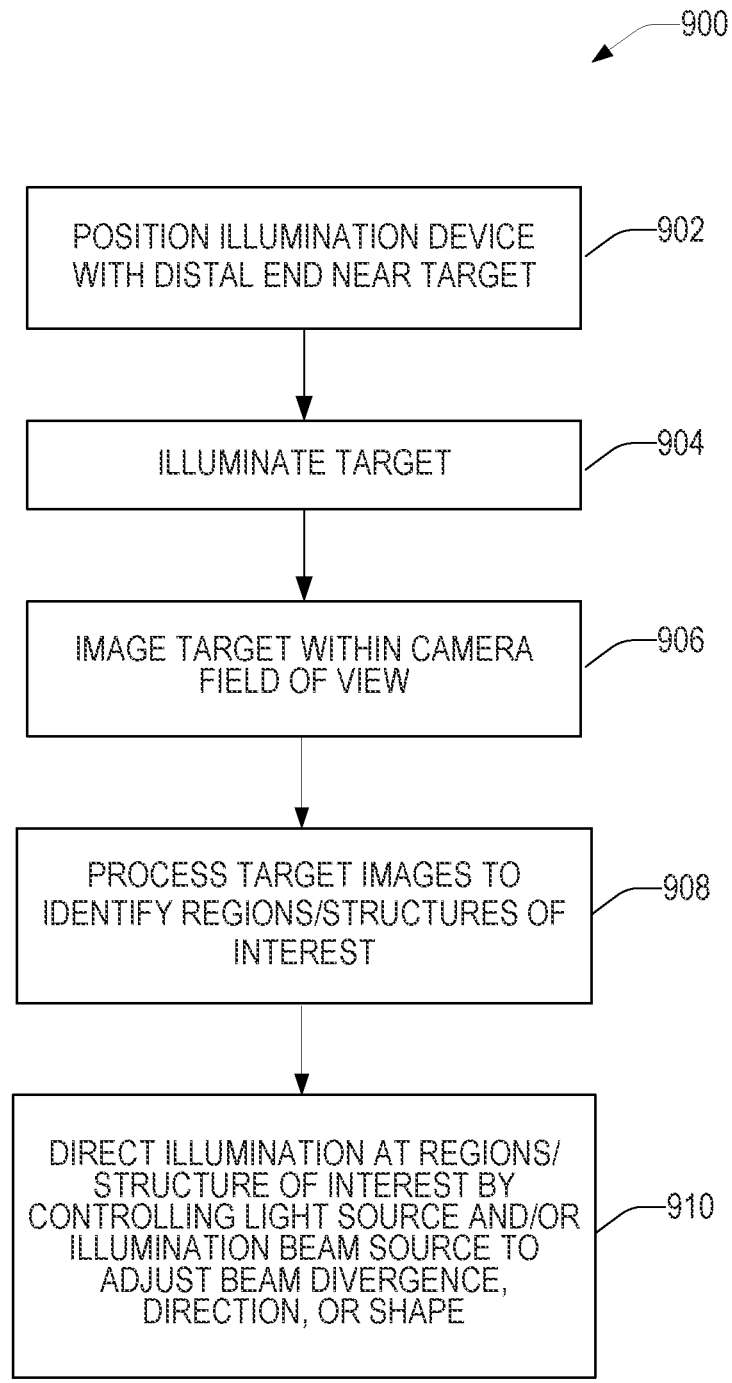
FIG. 9 is a flow chart of a method for illuminating a target with a beam of variable divergence, shape, or direction, in accordance with various examples.

FIG. 9 is a flow chart of a method 900 for illuminating a target with a beam of variable divergence, shape, or direction, in accordance with various examples. The method 900 may optionally begin with positioning the distal of an illumination device 102 (e.g., device 202, 602, 804) near a target (act 902). The target may be illuminated with a beam of light (e.g., illumination beam 224) emanating from the distal end of the illumination device 102 (act 904). The method 900 may optionally include imaging the target with one or more cameras 110 (which may, but need not, be integrated with the illumination device 102) within a field of view (act 906). The camera images are then optionally processed, e.g., by an image processor 116, and optionally with feedback received via a user interface 118, of a system controller an data processor 122, to determine one or more regions of interest within the field of view (act 908). The beam divergence, beam shape, and/or direction of the illuminating beam of light 224 relative to the optical axis at the distal end may be dynamically controlled, e.g, using any of the approaches discussed with reference to FIGS. 3A-8, to direct the light at the determined regions of interest (act 910) in order to concentrate the light in those regions. In various examples, illumination control may involve maintaining, regardless of the intensity distribution of the illumination beam, the total optical power output at the distal end of the illumination device below a threshold. The threshold may be a safety threshold, and keeping the optical power below the threshold may serve to avoid damage to the target or some structure in its vicinity (e.g., due to burning) in the event of an accidental physical contact with the distal end of the illumination device. Alternate to controlling total optical power output, a maximum optical power density (a local quantity) can be specified, and the system can control illumination to maintain the optical power density below the maximum optical power density.

The regions of interest can be determined (in act 908) in various ways based on various criteria, depending on the application. In some examples, the regions of interest are determined based on manual input from a human operator of the illumination device who views the images of the target (e.g., in the form of a continuous video stream) within the user interface. The user may, for example, zoom in and out of the field of view, or move a zoomed-in region relative to the field of view, and the illumination beam may be controlled to automatically adjust in location and/or size of the beam spot to the region selected by the user. Thus, zooming in the user interface, in some examples, can be accompanied by a change in the illumination beam divergence, and a change in location of the zoomed-in region relative to the field of view can result in a change in the illumination beam direction, to focus the light predominantly in the zoomed-in region. In this manner, the illumination can be dynamically matched to the region the operator is currently viewing. Another example of human input involves a user specifically selecting or outlining a structure or region of interest (e.g., in the context of endoscopy, a specific anatomic structure) in the user interface. The user may, for instance, use a mouse or similar cursor control device, a touch screen, or any other input device, to define the contours of the structure or region of interest directly. Alternatively, user input may be used in conjunction with some automated image analysis, e.g., to automatically identify structures (e.g., using edge detection or machine learning algorithms) and allow user selection, e.g., by clicking on one or more structures of interest. In either case, light may subsequently be concentrated in or on the selected regions and structures of interest, which may involve dynamically changing the direction or shape of the illumination beam as the illumination beam source at the distal end of the illumination device moves relative to the target.

In some examples, the regions are determined automatically based on specified criteria, and without further user input. For example, the images may be analyzed to determine the SNR as a function of location, and the illumination may be selectively increased in regions where the SNR falls below a specified threshold. Conversely, image analysis may identify saturated image regions, and illumination may be selectively decreased in those regions. As another example, depth analysis of the target may be performed, e.g., from pairs of images using any suitable stereo imaging technique, and the fall-off in illumination intensity with the square of the distance from the light source may be compensated for by increasing the illumination towards greater depth. Other criteria and ways of automatically analyzing the images and adjusting illumination based thereon may occur to those of ordinary skill in the art.

While the disclosed subject matter has been described and explained herein with respect to various examples, these examples are intended as illustrative only and not as limiting Various modifications, additional combinations of features, and further applications of the described examples that do not depart from the scope of the subject matter may occur to those of ordinary skill in the art. Accordingly, the scope of the inventive subject matter is to be determined by the scope of the following claims and all additional claims supported by the present disclosure, and all equivalents of such claims.

The invention claimed is:

1. A method comprising:
    illuminating a target with a beam of light emanating from
        a distal end of an illumination device that includes one or more optical fibers extending from a proximal end of the illumination device to the distal end by coupling light from a light source into the one or more optical fibers at the proximal end;

imaging the target within a field of view;

based on the imaging, determining one or more regions of interest within the field of view; and dynamically controlling an intensity of the light coupled from the light source into the one or more optical fibers as a function of input angle, to thereby control an angular intensity distribution of the beam of light relative to an axis of the illumination device at the distal end to direct the beam of light at the one or more regions of interest.

2. The method of claim 1, wherein controlling the intensity of the light coupled into the one or more optical fibers as a function of input angle comprises:

adjusting a programmable spatial filter in the light source.

3. The method of claim 1, wherein the one or more regions of interest are determined based on manual input from an operator of the illumination device viewing one or more images of the target within a user interface.

4. The method of claim 1, wherein determining the one or more regions of interest within the field of view comprises automatically analyzing one or more images of the target to identify one or more anatomic structures of interest and defining the one or more regions of interest based on the one or more anatomic structures of interest.

5. The method of claim 1, wherein determining the one or more regions of interest within the field of view comprises automatically analyzing a signal-to-noise ratio across one or more images of the target and defining the one or more regions of interest based on the signal-to-noise ratio.

6. The method of claim 1, wherein determining the one or more regions of interest within the field of view based on the imaging comprises automatically determining depth across the field of view and defining the one or more regions of interest based on the depth.

7. A system comprising:

one or more optical fibers comprising a proximal end and a distal end;

a light source configured and operable to couple light into the one or more optical fibers at the proximal end with an intensity controllable as a function of input angle to create a beam of light emanating from the one or more optical fibers at the distal end with an adjustable angular intensity distribution; and a controller configured to operate, based on one or more images of a target acquired by a camera, the light source to adjust the angular intensity distribution of the beam of light to direct the beam of light emanating from the one or more optical fibers at one or more regions of interest within a field of view of the camera.

8. The system of claim 7, further comprising a shaft housing the camera at a distal end of the shaft and housing the one or more optical fibers.

9. The system of claim 7, wherein the light source comprises a programmable spatial filter controllable to control the intensity of the light coupled into the one or more optical fibers at the proximal end as a function of input angle.

10. The system of claim 7, wherein the light source comprises a plurality of light emitters associated with different respective input angles of the light coupled into the one or more optical fibers, selectively operable to control the intensity of the light coupled into the one or more optical fibers at the proximal end as a function of input angle.

11. The system of claim 7, wherein the light source comprises a light emitter of variable intensity and a beam sweeper controllable to scan an input beam of light generated by the light emitter across a range of input angles into the one or more optical fibers as the intensity of the light emitter is being adjusted to thereby control the intensity of the light coupled into the one or more optical fibers at the proximal end as a function of input angle.

12. The method of claim 1, wherein controlling the intensity of the light coupled into the one or more optical fibers as a function of input angle comprises selectively operating a plurality of light emitters of the light source that are associated with different respective input angles of the light coupled into the one or more optical fibers.

13. The method of claim 1, wherein controlling the intensity of the light coupled into the one or more optical fibers as a function of input angle comprises adjusting an intensity of a light emitter of the light source while scanning an input beam of light generated by the light emitter across a range of input angles into the one or more optical fibers.

* * * * *